United States Patent [19]

Auth et al.

[11] Patent Number: 4,691,703

[45] Date of Patent: Sep. 8, 1987

[54] THERMAL CAUTERY SYSTEM

[75] Inventors: David C. Auth, Redmond; Dale M. Lawrence, Lynnwood; Tim R. Majoch, Kent, all of Wash.

[73] Assignee: Board of Regents, University of Washington, Seattle, Wash.

[21] Appl. No.: 856,573

[22] Filed: Apr. 25, 1986

[51] Int. Cl.$^4$ ............................................. A61B 17/36
[52] U.S. Cl. ................................. 128/303.1; 219/229; 219/241; 219/501
[58] Field of Search ........... 128/303.1, 303.13, 303.14, 128/303.17, 303.18, 399–401; 219/225, 230, 233, 240, 241, 242, 501

[56] References Cited

U.S. PATENT DOCUMENTS

| | | | |
|---|---|---|---|
| 3,358,152 | 12/1967 | Alexakis | 219/501 X |
| 4,301,357 | 11/1981 | Huffman | 219/240 X |
| 4,449,528 | 5/1984 | Auth et al. | 128/303.1 |

Primary Examiner—Lee S. Cohen
Attorney, Agent, or Firm—Seed and Berry

[57] ABSTRACT

A thermal cautery system having an endoscopically deliverable probe connected to a power supply and display unit. The power supply and display unit, when triggered by a footswitch, energizes a voltage regulator having a current limited output that supplies power to the probe. The current limiting function of the voltage regulator is disabled for a predetermined period that power is initially applied to said probe to minimize the heating time of said probe. The current through said probe is sensed and used to increase the voltage at the output of the voltage regulator as the current increases to compensate for the voltage drop in the conductors connecting the probe to the power supply. A manually selected portion of the sensed current through the probe is also integrated and used to terminate the flow of current through the probe when the integral of the current with respect to time has reached a predetermined value. A tone generator provides an audible indication when power is being applied to the probe and for a predetermined period thereafter to allow the probe to cool before the absence of the tone signals the removal of the probe from tissue being coagulated. The probe is heated by current flowing through an internal diode having a predetermined breakdown voltage at a predetermined temperature. The temperature of the probe is self-regulated by applying a voltage to the probe that is substantially equal to said predetermined voltage so that the current through the probe is reduced at said predetermined temperature.

9 Claims, 13 Drawing Figures

THERMAL CAUTERY SYSTEM

DESCRIPTION

The invention described herein was made in the course of work under a grant or award from the United States Department of Health, Education and Welfare.

1. Technical Field

This invention relates to the coagulation of vascularized tissues, and more particularly, to a thermal cautery system having a power supply and display unit connected to a miniaturized thermal cautery probe which is endoscopically deliverable.

2. Background Art

The use of heat for the cauterization of bleeding wounds dates back to ancient times. Perhaps the simplest and most basic thermal cauterization technique involves the application of a hot iron to a bleeding wound. While this technique is somewhat effective in cauterizing large, external wounds, the technique is not applicable to internal wounds. Nor is the technique sufficiently precise or delimited to provide adequate cauterization without excessive tissue damage.

In the present century, the use of radio frequency electric current traveling through a portion of the body has been widely used to stop bleeding. The essential ingredient in radio frequency cauterization is the dissipation of electrical energy in resistive tissue. This dissipated electrical energy is converted into heat, which produces a rise in temperature of the tissue and blood. The plasma proteins in blood are denatured in a temperature range of from 50° to 100° C., producing a sticky or congealed mass of proteins. This process is familiar in the cooking of egg white. Other processes may take place when tissue is heated. For example, vessels may contract or shrink, thereby further reducing the flow of blood.

Several radio frequency current generators are now commercially available and are widely used by surgeons for both cutting and coagulating tissue. Since the electrical current flow follows the path of least resistance, the resulting thermal damage, or necrosis, may at times be unpredictable, too deep, and uncontrolled. The rationale for using radio frequency current to control bleeding is that the frequency is above that which would cause neuromuscular stimulation and yet permits sufficient power dissipation to produce a rapid rise in temperature. Thus, used properly, electrical shock does not occur and coagulation is accomplished.

There is currently much interest in the control of bleeding using the modern fiberoptic endoscope, which permits visualization and therapy in hollow organs of the body through a slender tube. Hollow channels with a few millimeters of inside diameter permit the insertion of instruments for the administration of therapy, such as the coagulation of bleeding. Some investigators have reported good success in using radio frequency coagulation through the endoscope in a clinical setting. But this technique has not been widely used because of its inherent risks. Several groups have directed a laser beam through an endoscope using a special optical wave guide with good success in both animals and humans. However, the high cost of laser coagulators and the as-yet unproven benefit in a controlled clinical trial are slowing the widespread adoption of this technique. Other problems associated with laser coagulators arise from the difficulty in precisely directing the laser beam to a moving target, the existence of optical hazards, and the need for a gs injection system to wash away overlying blood. Furthermore, simple laser coagulators do not simultaneously apply heat and pressure to the wound; and the combination of heat and pressure is considered to be more effective than heat alone.

More recently, a miniaturized thermal probe has been developed which is endoscopically deliverable. This probe, which is described in an article by Protell et al., "The Heater Probe: A New Endoscopic Method for Stopping Massive Gastro-Intestinal Bleeding," *Gastroenterology* 74: 257-62 (1978), includes a heating coil mounted in a small cylindrical body with a thermocouple. The output of the thermocouple is compared to a temperature reference level, and the difference is used to control the power to the probe to achieve a preset probe temperature. In use, the probe is heated to the preset value and applied to the wound for a number of predetermined periods. Alternatively, the cold probe is applied directly to the bleeding site, turned on, and held there for a predetermined period after reaching a target temperature. The principal problem associated with the latter technique is the inability of the probe to reach coagulating temperature with sufficient speed and to then cool itself with sufficient speed to prevent excessive penetration of the heat by diffusion. Effective coagulation requires that the bleeding site be adequately heated. However, avoidance of thermal necrosis requires that the heat not penetrate too deeply.

The only technique providing adequate heating of the bleeding site without producing excessive heat penetration is heating the bleeding site at a high temperature for an extremely short period of time. Presently existing thermal probes are not able to meet these requirements. The problem does not stem from an inability to heat the probe with sufficient speed as much as it does from an inability to cool the probe with sufficient speed. Any probe can be heated rapidly by merely utilizing a sufficiently large heater. However, the probe can be cooled only by the tissue witch which it is in contact. Conventional probes have been incapable of being cooled by the surrounding tissue with sufficient speed due to their relatively high thermal mass.

Attempts have been made to design thermal cautery probes which are heated by passing a current through the body of the probe itself of through a separate heating element. An example of such probes is disclosed in U.S. Pat. No. 3,886,944, issued to Jamshidi. The disadvantages of such probes are twofold: first, the unavailability of a satisfactory probe material, and second, the nonuniformity of the probe temperature.

The choice of a probe material presents a problem because the resistance of the material must be high enough to dissipate sufficient power and the strength of the material must be high enough to withstand forces applied to the probe by the tissue and other objects. The Jamshidi probe utilizes a Nichrome alloy or stainless steel as the probe material. Either material has a relatively low resistivity, thereby making it difficult for the probe to dissipate sufficient power without applying a great deal of current to the probe. While probes requiring high current are acceptable under some circumstances, they are unacceptable where the probe is to be endoscopically deliverable, since the high currents require wires which are larger than the endoscope channels. In fact, a probe having a resistance less than about 0.5 ohm will generally require more current than endoscopically deliverable power leads are capable of carrying.

A probe fabricated of a low-resistivity material can dissipate adequate power from relatively low current only by making the material extremely thin so that the resistance of the probe is high. Yet a probe having an extremely thin shell does not have sufficient strength to withstand clinical use.

A probe having a relatively thick shell of a higher resistivity or semiconductive material would be capable of dissipating adequate power at acceptably low currents. However, a material which has these properties and which is inexpensive, easily worked, and sufficiently sturdy does not appear to be availabe.

The second disadvantage mentioned above, the nonuniformity of probe temperature, is illustrated in the Jamshidi patent. In the Jamshidi probe, current flows outwardly from the center of the probe tip and then along the sides of the probe. The current density, and hence the power dissipation, vary from a maximum at the center of the probe to a minimum at the sides of the probe. As a result, the temperature of the probe decreases from a maximum at the center of the probe.

One thermal cautery probe design that solves many of the aforementioned problems is described in U.S. Pat. No. 4,449,528, to Auth et al. The cautery probe described in the '528 patent utilizes a heating element having a low thermal mass so that it may be quickly heated. Yet it quickly cools when power is removed from the probe. One disadvantage of the thermal cautery probe described in the '528 patent is the complexity of the circuit controlling the temperature of the probe. Basically, a predetermined quantity of energy is delivered to the probe, although the voltage across the diode heating element is monitored to determine the temperature of the probe. This voltage is compared to a reference voltage corresponding to a predetermined temperature. If the voltage across the diode exceeds the reference voltage, the circuitry terminates the supply of energy to the probe.

DISCLOSURE OF THE INVENTION

The primary object of the invention is to provide a thermal cautery probe that can be maintained at a predetermined temperature without the use of a complex power supply unit.

These and other objects of the invention are provided by a thermal cautery system including a thermal cautery probe connected to a power supply. The thermal cautery probe includes a diode mounted in the probe in thermal contact with a heat-transfer portion that is adapted to be placed in contact with the tissue to be cauterized. The diode has a predetermined breakdown voltage at a predetermined temperature. The power supply applies an output voltage to the diode that is substantially equal to the predetermined breakdown voltage so that the current through the diode is relatively large when power is initially applied to the probe. However, as the temperature of the probe approaches the predetermined temperature, the flow of current through the diode is inherently reduced by the reduced voltage differential between the power supply and the breakdown voltage of the diode. As a result, the temperatur of the diode is automatically regulated at the predetermined temperature without the use of a complex and expensive feedback circuit. A resistor may be connected in series between the power supply and the diode to limit the current through the diode when power is initially applied to the diode.

BEST MODE FOR CARRYING OUT THE INVENTION

Figure 1:
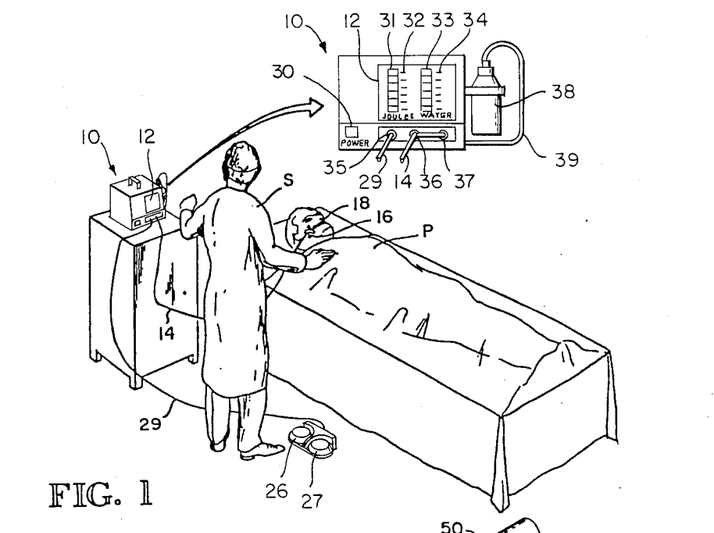
FIG. 1 is an isometric view of the thermal cautery system in operation.

The thermal cautery system is illustrated in use in FIG. 1. The system includes a power supply and display unit 10 having a front panel 12 containing switches and indicators (illustrated in greater detail in the enlarged view). A specially constructed catheter 14 extends from the power supply and display unit 10 to a headpiece 16 of a conventional fiberoptic endoscope 18 extending into the mouth of a patient P to, for example, the patient's stomach. The headpiece 16 typically includes an eyepiece through which a surgeon S views internal cavities. However, the headpiece 16 may alternatively interface with various optical devices of conventional design. The endoscope 18 typically includes one or more passages or channels extending in parallel with the fiberoptic wave guide to allow various devices to be inserted into internal organs of a patient. The catheter 14 extends through one of these channels to the end of the endoscope 18 within an internal organ. A surgeon S may then position the probe 22 against a lesion, such as an ulcer, by manipulating actuator knobs generally positioned on the headpiece 16 of conventional endoscopes 18. The endoscope channels are necessarily limited in diameter so that the diameter of the power leads for applying power to the probe are also limited. In practice, the diameter of the power leads is limited to a size that is capable of delivering sufficient current for cauterization to a probe having a resistance of at least about 0.5 ohm. A probe having a lower resistance must receive a current which is in excess of that which endoscopically deliverable power leads are capable of efficiently carrying without producing excessive heating of the endoscope.

A pair of foot switches 26, 28 are also connected to the power supply and display unit 10 through a multiconductor cable 29. As explained in greater detail hereinafter, the surgeon S actuates the first foot switch 26 to apply power to the probe 22 after the probe has been applied to the lesion. The second switch 28 is actuated to supply a washing fluid to the probe.

As best illustrated in the enlarged view of FIG. 1, the panel 12 includes an on/off switch 30 for applying power to the unit 10. The panel 12 also includes a touch-switch panel 31 for selecting the energy to be delivered to the probe each time the foot switch 26 is pressed. A set of indicator lamps 32 provides a visual display of the energy level that has been selected on the panel 31. A similar touch-switch panel 33 is used to select the pressure of wash water supplied to the probe 22, as described in greater detail below. The selected wash pressure is displayed by the indicator lamps 34. The cable 29 from the foot switches 26, 28 plugs into jack 35. The electrical conductors of the catheter 14 plug into jack 36, while the wash water is delivered through outlet 37. The wash water is stored in an autoclavable container 38 and is supplied to the power supply and display unit 10 through conduit 39.

Figures 2, 3:
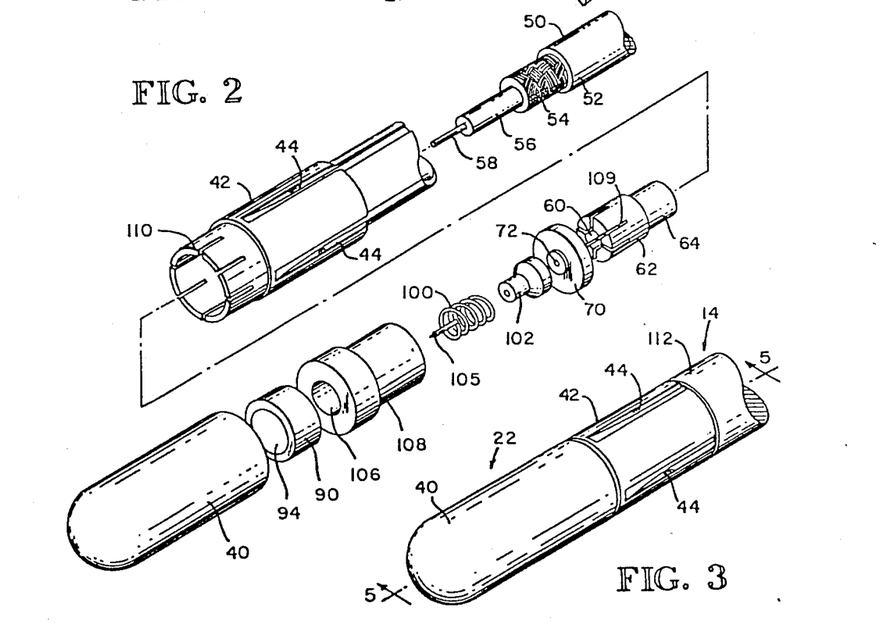
FIG. 2 is an exploded isometric view of the thermal cautery probe used in the thermal cautery system of FIG. 1.
FIG. 3 is an isometric view of the assembled thermal cautery probe.

The probe 22 is illustrated in assembled condition in FIG. 3. It is composed of an elongated cylindrical shell 40 having a smooth, round-ended forward portion and a cylindrical body 42 containing a number of circumferentially spaced-apart cleaning fluid nozzles 44. The catheter 14 abuts the body 42 of the probe 22 and supplies cleaning fluid to the nozzles 44 and heating pulses to an internal heating element in the shell 40, as explained in greater detail hereinafter.

Figure 4:
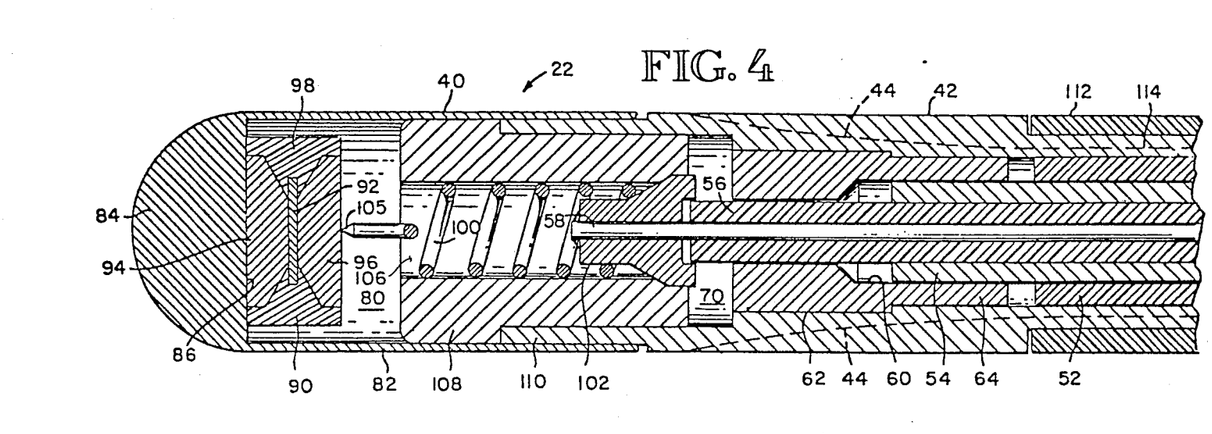
FIG. 4 is a cross-sectional view taken along the line 4—4 of FIG. 3.

The internal structure of the probe 22 is illustrated in greater detail in FIGS. 2 and 4. This structure is best explained in the context of the manufacturing procedure for the probe. Initially, a coaxial cable 50 is prepared by trimming a portion of an insulating sheath 52 back from an underlying coaxial metal braid 54, a coaxial dielectric insulator 56, and a center conductor 58. In a similar manner, the braid 54 is trimmed back from the underlying insulator 56 and conductor 58, and the insulator 56 is trimmed back from the underlying conductor 58. As a result, each component of the cable 50 is accessible.

After the cable 50 has been prepared as explained above, the body 42 of the probe 22 is loosely slipped over the cable 50, and the insulator 56 and center conductor 58 are inserted through a bore 60 of a coaxial braid anchor 62, with the braid 54 loosely fitting inside a cylindrical portion at the rear of the braid anchor 62. The braid 54 is then soldered to the walls of the bore 60 by conventional means to electrically and mechanically connect the braid anchor 62 to the braid 54 of cable 50.

A spring mount 102 is then soldered to the center conductor 58 of the coaxial cable 50, and a spring 100 is soldered onto the spring mount 102. Next, the braid anchor 62 is slipped into the body 42, with resilient fingers 109 of the braid anchor 62 frictionally engaging the inside surface of the body 42. Next, the assembly is placed in a vertical position and a small amount of epoxy is applied between spring mount 102 and braid anchor 62 to form a seal 70 having a shoulder 72. The seal provides electrical insulation and prevents fluids from entering the internal cavity of the probe. A Teflon ® seal 108 is then pressed into body 42, with the shoulder on seal 108 resting against the fingers 110 of body 42. The spring 100 now lies inside of the cylindrical bore 106 of seal 108, with the axial tip 105 of spring 100 protruding from the bore 106 of a small amount.

After the rearward components of the probe 22 are prepared and assembled as explained above, the internal components of the shell 40 are assembled. As best illustrated in FIG. 4, the shell 40 is generally hollow to form a cylindrical cavity 80 surrounded by thin, cylindrical sidewalls 82. The front end of the shell 40 is a solid hemispherical heat-transfer portion 84 having a planar, circular rear face 86. A controlled breakdown diode, such as a Zener or avalanche diode 90, is then bonded within the cavity 80 against the rear face 86.

The diode 90 is mounted in the shell 40 by first tinning the rear face 86 of the heat-transfer portion 84 with solder. The exposed surface of one diode conductor 94 is then also tinned and placed in the shell 40, preferably using an alignment jig to position the diode 90 at the center of the shell 40. The shell 40 is then heated to fuse the solder on the rear face 86 and the solder on the diode conductor 94. The diode 90 is thus in direct thermal contact with the heat-transfer portion 84 so that heat is transferred from the diode 90 to the heat-transfer portion 84 principally by conduction rather than by radiation.

After the diode 90 is soldered within the shell 40, the outer surfaces of the shell 40 are polished and then plated with copper and gold. Finally, a conformal coating is applied to the outer surface of the shell 82 to prevent it from sticking to tissues after coagulation. The coating may be Type R-4-3117 sold by Dow-Corning, which is normally used to seal printed circuit boards from moisture and abrasion. The coating should be applied over an undercoat of Dow-Corning 1204 Primer for best adhesion of the conformal coating to the probe. Alternatively, the primer may be used without the conformal coating, providing the probe with better heat transfer characteristics to tissue but having a greater tendency to adhere to coagulated tissues.

In a final assembly stage, the shell 40 is moved rearwardly until resilient fingers 110 of the body 42 frictionally engage the inner walls 82 of the shell 40. Finally, as illustrated in FIGS. 3 and 4, a catheter 112, loosely surrounding the cable 50, is slipped onto a shoulder 114 (FIG. 4) formed along the rear edge of the body 42, thereby completing the assembly of the probe.

A washing fluid is pumped through the catheter 112 around the cable 50 and enters rear openings of the nozzles 44. The washing fluid then flows along the side of the shell 40 in an axial direction to wash blood from the lesion, thereby facilitating the identification of bleeding sites in need of coagulation. A variety of commercially available pumps may be used to deliver washing fluid to the probe. However, the fluid is preferably delivered in a pulsating fashion to allow sufficient bleeding between washing pulses to make the site of bleeding readily visible.

It is highly advantageous to run the washing fluid along the outside of the shell for a number of reasons. First, the washing fluid does not pass between the heat-transfer portion 84 of the probe and the tissue to be coagulated. Consequently, it does not interfere with the transfer of heat from the probe to the tissue. Second, the washing fluid flows along surfaces which do not contact tissue and are thus not susceptible to tissue clogging, which would interfere with fluid flow. Finally, the fluid stream is spread out over a sufficiently large area to prevent tissue damage which might otherwise occur with a more concentrated fluid stream.

In the probe's assembled condition, the conductor spring 100 is somewhat compressed so that the point 105 forcibly contact the conductor 96. The diode conductor 94 is connected to the shell 40 and, in turn, to the braid 54 through the body 42 and braid anchor 62. Thus, as current pulses are applied between the center conductor 58 and the braid 54 of cable 50, current flows through the semiconductor junction 92, which quickly heats the heat-transfer portion 84. The heat-transfer portion 84 preferably has a low heat capacity so that the portion 84 not only quickly rises to a target temperature, but it also quickly cools after heating pulses are no longer applied to the probe 22.

Figure 5:
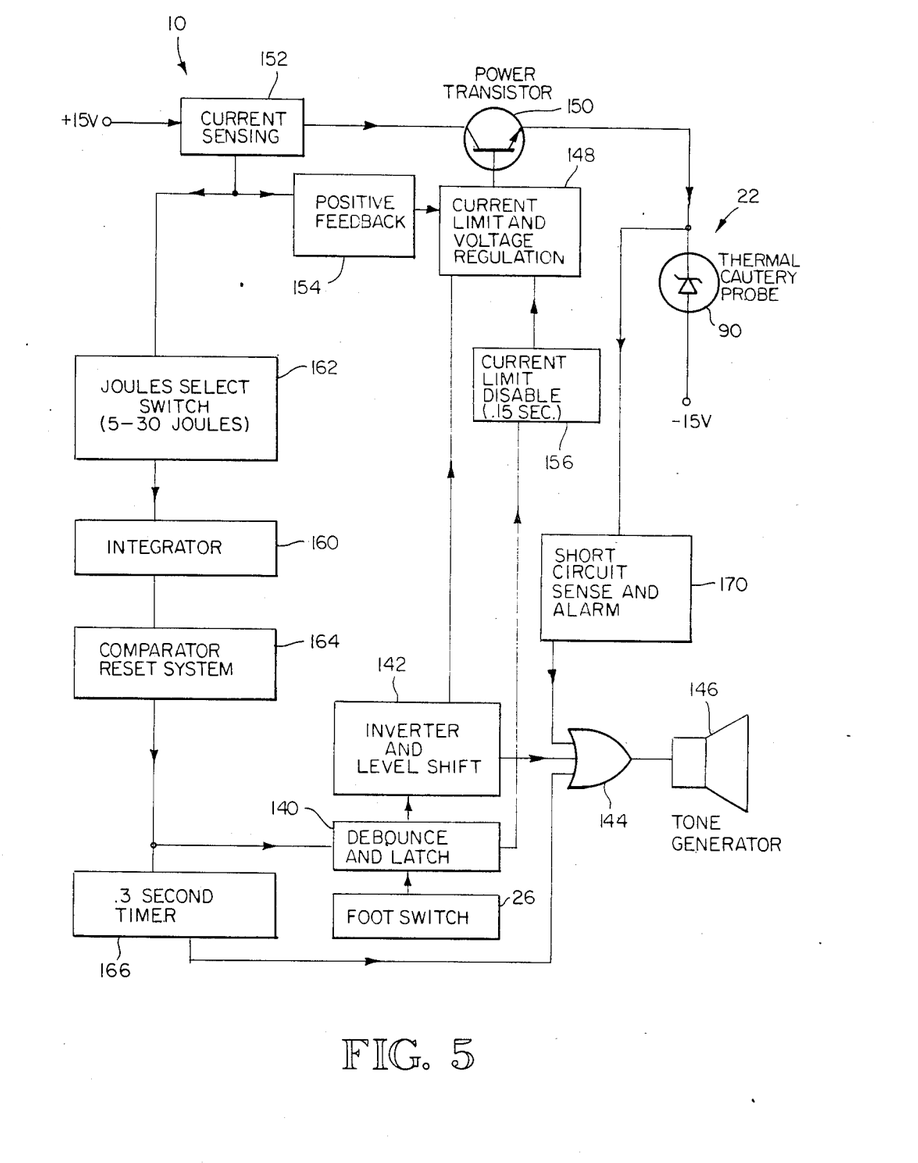
FIG. 5 is a block diagram of the power supply and display unit that is connected to the thermal cautery probe.
Figure 6A:
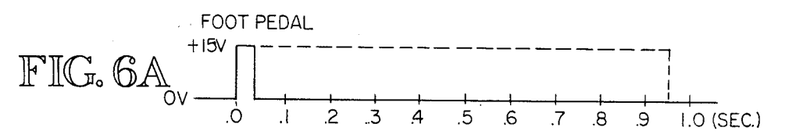
FIG. 6 is a timing diagram showing various waveforms in the block diagram of FIG. 5.

The power supply and display unit 10 is illustrated in block diagram form in FIG. 5. When the foot switch 26 is actuated, a signal illustrated in FIG. 6A is applied to a debounce-and-latch circuit 140, which ensures that the power supply and display unit 10 is not actuated twice because of intermittent contact in switch 26. The debounce-and-latch circuit 140 remains energized until it is reset, as explained in greater detail below.

Figure 6B:
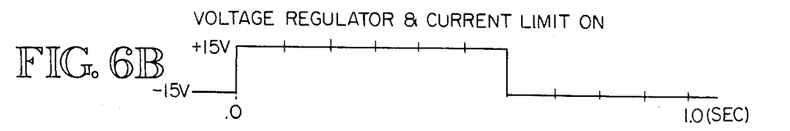

Triggering the debounce-and-latch circuit 140 to its energized condition generates two outputs. The first output is applied to an inverter and level-shift circuit 142 that, in turn, generates two outputs. The first output is applied to an OR-gate 144, which then energizes a conventional tone generator 146. The second output of the inverter and level-shift circuit 142 energizes a currentlimit and voltage-regulation circuit 148, which, as explained in greater detail below, causes power to be applied to the thermal cautery probe 22. Basically, the current- limit and voltage-regulation circuit 148 applies a high to power transistor 150, thereby causing current to flow from a +15 volt source through a current-sensing circuit 152 and through the diode 90 in the probe 22 to a −15 volt supply. The output of the current limit and voltage regulation circuit 148 is illustrated in FIG. 6B.

The output of the current-sensing circuit 152 is applied to a positive-feedback circuit 154. The purpose of the positive-feedback circuit 154 is to increase the applied voltage with increasing current in order to compensate for the voltage drop in the line connecting the power transistor 150 to the diode 90. Thus, the voltage drop in the line connecting the power transistor 150 to the diode 22 is compensated for by the positive-feedback circuit 154 in combination with the current-limit and voltage-regulation circuit 148.

Figure 6C:
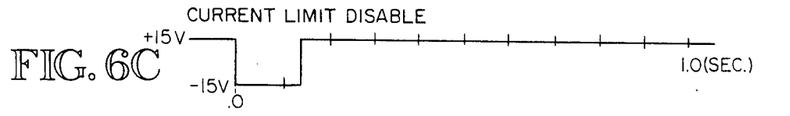

As explained above, the debounce-and-latch circuit 140 generates two outputs, the first of which is applied to the inverter and level-shift circuit 142. The second output of the debounce-and-latch circuit 140 is applied to a current-limit disable circuit 156, which generates an output, as illustrated in FIG. 6C, that is applied to the current-limit and voltage-regulation circuit 148. The output of the current-limit disable circuit 156 disables the current-limiting function of the current-limit and voltage-regulation circuit 148 for the first 150 milliseconds of the period that energy is applied to the probe 22 in order to minimize the heating time of the probe 22.

Figure 6D:
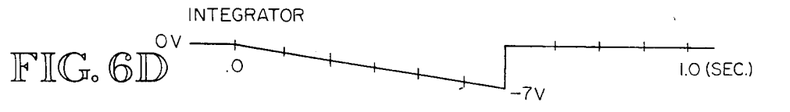

In addition to supplying an output to the positive feedback circuit 154, the current-sensing circuit 152 also applies an output to an integrator 160 through the Joule select-switc circuit 162. Basically, the Joule select-switch circuit 162 controls the percentage of the signal generated by the current-sensing circuit 152 that is applied to the integrator 160. A higher energy level selected on teh switch panel 31 (FIG. 1) reduces the percentage of the output of the current-sensing circuit 152 that is applied to the integrator 160. The magnitude of the signal applied to the integrator circuit 160 is thus a function of both the magnitude of the current applied to the probe 22 and the energy level selected on the switch panel 31. A higher energy level allows more current to flow to the probe 22 before the output of the integrator 160 has reached a predetermined value. The output of the integrator 160 is illustrated in FIG. 6D for a constant current applied to the thermal cautery probe 22.

Figure 6E:
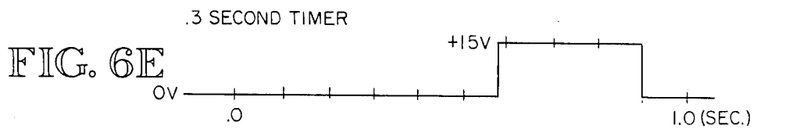
Figure 6F:
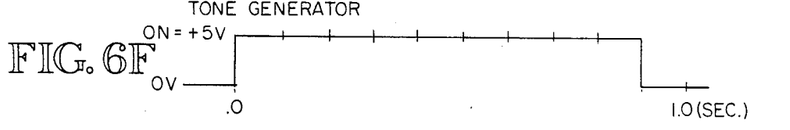

When the output of the integrator 160 reaches a predetermined value, as determined by a comparator/reset system 164, the debounce-and-latch circuit 140 is reset and a 0.3 second timer 166 is triggered. The output of the timer circuit 166 energizes the tone generator 146 through OR-gate 144 in order to continue the tone 300 milliseconds after power is removed from the thermal cautery probe 22. This feature discourages the operator from removing the thermal cautery probe 22 from tissues being coagulated while it is still sufficiently hot to produce coagulation. After 300 milliseconds have elapsed, the probe has cooled sufficiently and the tone generator 146 is de-energized, thereby signaling the operator to remove the probe 22 from the tissues being coagulated. The output of the 0.3 second timer 166 is illustrated in FIG. 6E, while the input to the tone generator 146 is illustrated in FIG. 6F.

The power supply and display unit 10 also includes a short-circuit-sensing and alarm circuit 170. Basically, the short-circuit-sensing and alarm circuit 170 measures the voltage across the thermal cautery probe 22. When the voltage across the probe 22 falls to an abnormally low leve, the circuit 170 applies a signal to the tone generator 146 through the OR-gate 144. In order to distinguish the tone generated by a short circuit from a tone generated by normal operation of the unit, the signal generated by the short-circuit-sense and alarm circuit 170 is pulsating.

Figure 7A:
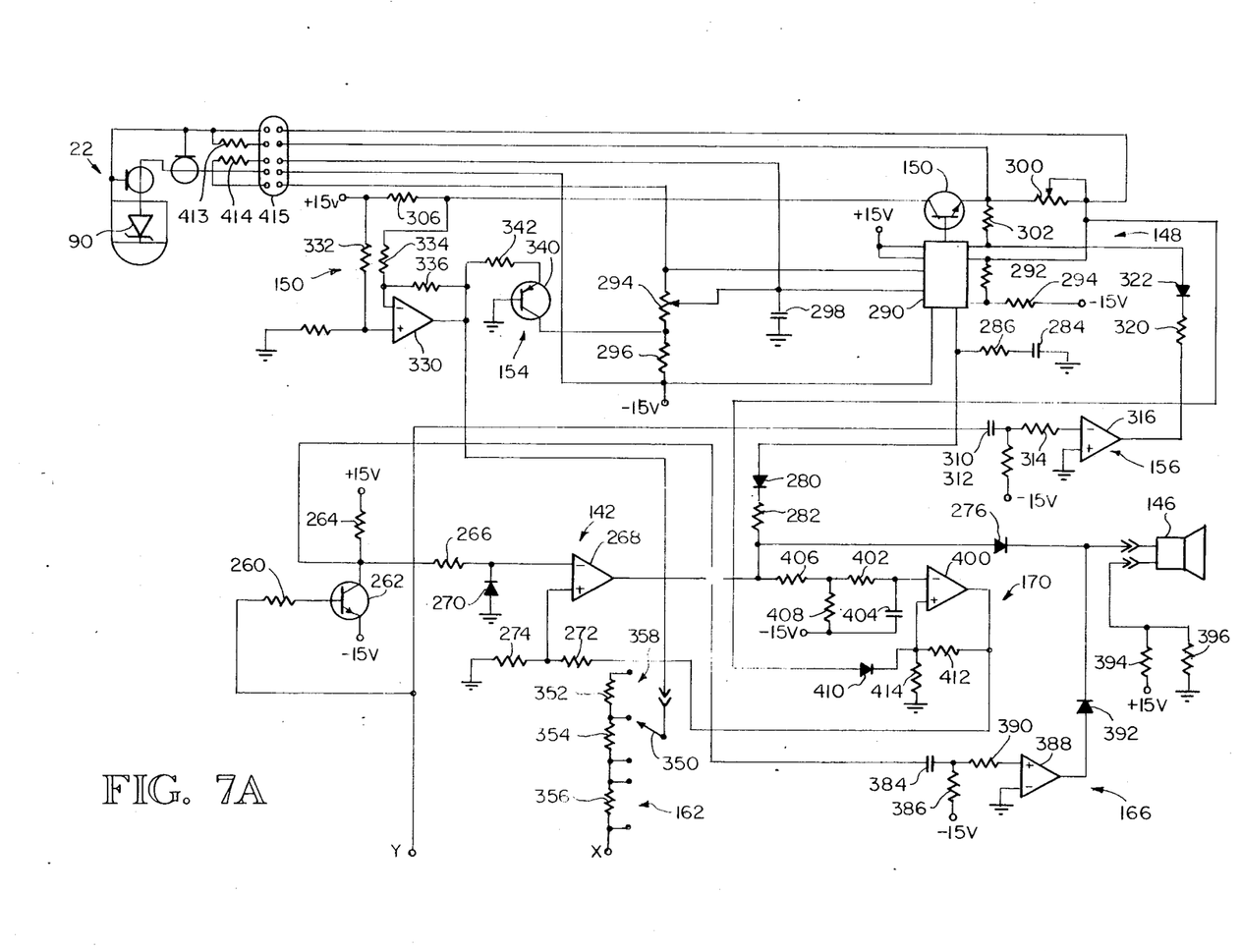
FIGS. 7A and 7B are schematics of the power supply and display unit of FIG. 5.
Figure 7B:
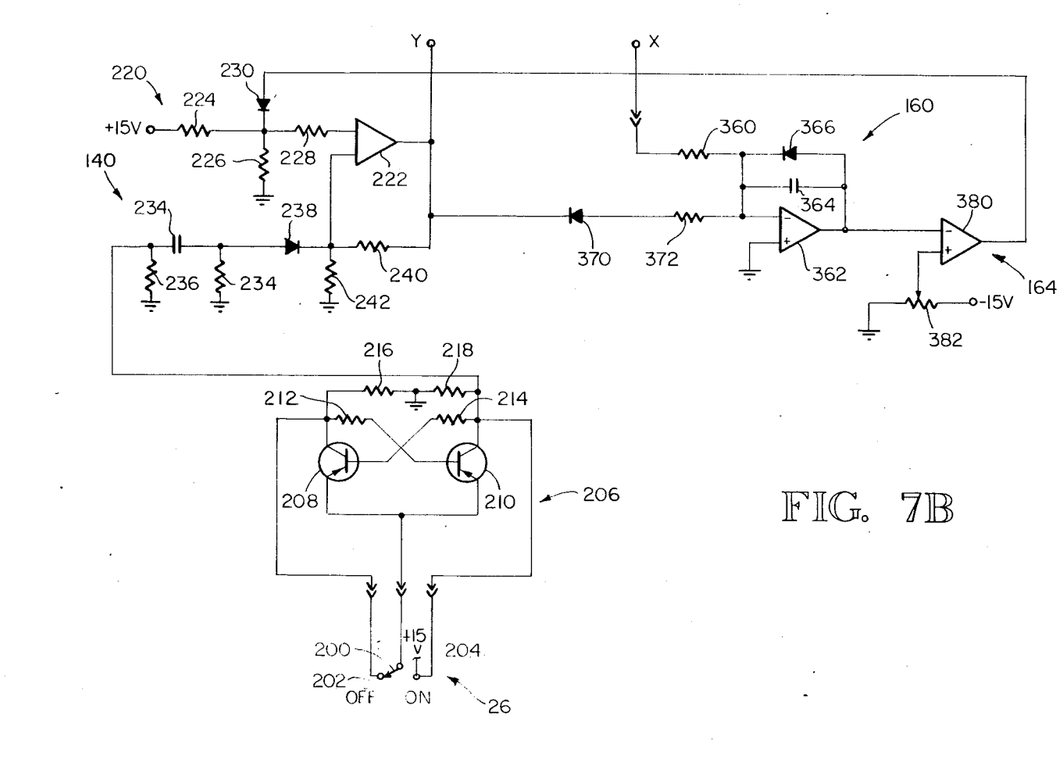

A schematic of the power supply and display unit of FIG. 5 is illustrated in FIG. 7. The foot switch 25 consists of a single-pole, double-throw switch of which the center contact 200 receives the positive supply voltage and the remaining contacts 202, 204 are connected to a flip-flop 206. The flip-flop 206 is of conventional design consisting of transistors 208, 210 and resistors 212–218. When the switch contact 200 is connected to the "off" switch contact 202, the positive supply voltage on the collector of transistor 208 is fed through resistor 212 to the base of transistor 210, thereby turning transistor 210 off. When transistor 210 is turned off, current flows from the base emitter junction of transistor 208 and resistors 214, 218, thereby turning on transistor 208, even if electrical contact 200 is no longer connected to the "off" electrical contact 202. When the switch contact 200 is switched to the "on" contact 204, the positive supply voltage is applied to the base of transistor 208 through resistor 214, thereby turning off transistor 208. Current then flows through the base emitter junction of transistor 210 and resistors 212, 216, thereby turning on transistor 210. The collector of transistor 210 is then pulled to substantially the positive supply voltage, thus maintaining transistor 208 cut-off and generating an actuating signal that is applied to a latch circuit 220. The flip-flop 206 is reset when the contact 200 is once again connected to the "off" contact 202 in the same manner that the flip-flop 206 becomes set, as described above.

The latch 220 includes a comparator 222 that receives a reference voltage generated by voltage divider resistors 224 and 226. This reference voltage is applied to the negative input of comparator 222 through resistor 228. The latch 220 is reset by a high applied through diode 230, as explained below. The positive-going pulse generated by the flip-flop 206 when the foot switch 26 is actuated to its "on" position is differentiated by capacitor 232 and resistor 234. Resistor 236 provides a discharge path for capacitor 232 at the termination of the positive-going pulse from the flip-flop 206. The differentiated output of the flip-flop 206 is applied through diode 238 to the positive input of the comparator 222. The differentiated leading edge of the positive-going pulse from the flip-flop 206 will normally exceed the voltage reference on the negative input of the comparator 222, thus causing the output of the comparator 222 to go positive. The positive output of the comparator 222 is applied to the positive input of the comparator 222 through feedback resistor 240, which, in combination withr esistor 242, forms a voltage divider. The divider ratio of the resistors 240, 242 is set so that the voltage applied to the positive input of the comparator 222 (generated from the output of the comparator 222) exceeds the reference voltage applied to the negative input of the comparator 222. The comparator 222 thus continuously generates a positive output until a positive-going reset signal is applied through diode 230, thereby making the negative input to the comparator 222 larger than the positive input to the comparator 222.

As explained above with reference to FIG. 5, the output of the debounce-and-latch circuit 140 is applied to the inverter and level-shift circuit 142 and to the current-limit disable circuit 156. The inverter and level-shift circuit 142 receives its inputs at the base of transistor 262 through resistor 260, thereby turning on transistor 262 and drawing current through load resistor 264. The collector of transistor 262 then switches from the positive supply voltage to the negative supply voltage, and this negative voltage is applied through resistor 266 to the negative input of a comparator 268. Diode 270 clamps the input to the comparator 268 at slightly less than zero volts so that the negative input to the comparator 268 varies between approximately zero volts and the positive supply voltage. The positive input to the inverter 268 normally receives a positive voltage from the short-circuit-sense and alarm circuit 170 and voltage divider resistors 272, 274, as explained in greater detail below. Thus, when the debounce-and-latch circuit 140 generates its positive-going output in response to actuation of the foot switch 26, the output of comparator 268 goes high.

The high at the output of the inverter and level-shift circuit 142 (i.e., comparator 268) actuates the tone generator 146 through diode 276. The high at the output of comparator 268 also back-biases diode 280 through resistor 282. Back-biasing diode 280 allows capacitor 284 to charge through resistor 286, thereby allowing a conventional LM723 voltage regulator 290 to apply a regulated voltage to the base of transistor 150. The voltage regulator 290 is connected in a conventional manner with a regulated 6.6-volt output being generated at pin 3, which is fed back to pin 4 through voltage divider resistors 292, 294. A voltage reference is applied to the voltage regulator 290 at pin 5, which is generated from pin 6, potentiometer 294, and voltage divider resistor 296. Capacitor 298 is provided to filter the voltage reference. The voltage applied to pin 5 of the voltage regulator 290 determines the voltage at the output of the voltage regulator 290 that is applied to the base of transistor 150. The voltage regulator 290 includes an internal current-regulating circuit. The current limit level is determined by potentiometer 300 which is applied directly to pin 3 of the voltage regulator 290 and to pin 2 through resistor 302.

As mentioned above with respect to FIG. 5, the current-limiting function of the voltage regulator 290 is disabled for the first 150 milliseconds of the probe energization by the current-limit disable circuit 156. The current-limit disable circuit 156 receives the positive-going pulse from the debounce-and-latch circuit 140. This pulse is differentiated by capacitor 310 and resistor 312. And applied through resistor 314 to the negative input of comparator 316. The time constant of capacitor 310 and resistor 312 is selected so that the negative input to the comparator 317 is positive for approximately 150 milliseconds. During this 150 millisecond period, the output of the comparator 316 is negative. This negative output is applied through resistor 320 and diode 322 to disable the current-limiting function of the voltage regulator 290 through pin 2 of the voltage regulator 290. At the end of 150 milliseconds, the output of the comparator 316 goes positive, thereby back-biasing diode 322 and allowing the voltage regulator 290 to perform its current-regulating function.

When the voltage regulator 290 turns on transistor 150, current flows from the positive supply voltage to the negative supplyv oltage in sequence through current-sensing resistor 306, transistor 150, current limit-sensing resistor 300, and diode 90 in the probe 22. The conductors connecting the power supply and display unit 10 to the probe 22 contain appreciable resistance due, in part, to their relatively small diameter. As explained above, the relatively small diameter of the wires is required to make the probe 22 endoscopically deliverable. The significant resistance of the conductors results in an appreciable voltage drop in the conductor. For this reason, as explained above, a positive-feedback circuit 154 is provided to increse the voltage generated by the voltage regulator 290 at high current levels.

The voltage across the current-sensing resistor 306, which is indicative of the current flowing through the diode 90, is applied differentially to an operational amplifier 330 through resistors 332, 334. The gain of the amplifier 330 is determined by the ratio of feedback resistor 336 to summing junction resistor 334, and, in one operational embodiment, is set to approximately 4, with the current-sensing resistor 306 being selected so that the output of the amplifier 330 is 8 volts per amp. The output of the amplifier 330 is applied to the collector of transistor 340 through resistor 342. The current flowing through transistor 340 is approximately equal to the ratio of the voltage at the output of amplifier 330 to the value of resistor 342. This current also, of course, flows through resistor 296, thereby increasing the voltage that is applied to pin 5 of the voltage regulator 290 through potentiometer 294. In this manner, the reference voltage applied to the voltage regulator 290 is increased with increasing current flows through the diode 90. This increased voltage is a function of increasing current and thus compensates for the voltage drop in the conductors connecting the power supply and display unit 10 to the probe 22.

The output of the current-sensing circuit 152 is also applied to the Joule select switch 162, as explained above withr eference to FIG. 5. The Joule select switch 162 consists of a single-pole, five-contact swtich 350 having resistors 352, 354, 356 connected between its contacts 358. The output of the current-sensing circuit 152 is applied through resistor 360 and possibly resistors 352-356 to an integrator consisting of operational amplifier 362 and capacitor 364. Diode 366 is provided to clamp the output of the opeational amplifier 362 to approximately zero volts so that the output of the amplifier 362 can only be negative. The uppermost positoin of the switch 350 corresponds to the maximum energy selected on the switch panel 31 (FIG. 1), while the lowermost position of the switch 350 corresponds to the five-Joule selection on the switch panel 31. Thus, selecting thirty Joules causes the integrator 160 to integrate at a slower rate, thus allowing a greater amount of current to flow through the diode 90 before the output of the operational amplifier 362 reaches a predetermined value. Conversely, selecting an energy level of five Joules causes the integrator 160 to integrate relatively rapidly, thus allowing the output of the operational amplifier 362 to reach a predetermined value after relatively little current has flowed through the diode 90.

The integrator 362 is reset through diode 370 and resistor 372 when the debounce-and-latch circuit 140 is reset, as explained above with reference to FIG. 5 and a explained below in greater detail with reference to FIG. 7. Specifically, when the debounce-and-latch circuit 140 is reset, the output of comparator 222 goes low, thereby discharging capacitor 364 through diode 370 and resistor 372. At the start of the next energization period for the probe 22, the output of the operational amplifier 222 goes high, thereby back-biasing the diode 370 and allowing the operational amplifier 362 to start integrating.

As explained above, the output of the operational amplifier 362 increases at a rate that is a function of both the integral of the current through the diode 90 and the position of the Joule select switch 350. The output of the opeational amplifier 362 is applied to the negative input of a comparator 380, while the positive input of the comparator 380 receives a reference voltage from potentiometer 382. When the output of the operational amplifier 362 has integrated negatively to the reference voltage from potentiometer 382, the output of the comparator 380 goes positive. The positive voltage at the output of the comparator 380 is applied to the comparator 222 of the debounce-and-latch circuit 140 through diode 230 and resistor 228. The positive voltage applied to the negative input of comparator 222 causes the output of comparator 222 to go negative, thereby unlatching the debounce-and-latch circuit 140 and maintaining the output of the comparator 222 low. This low at the output of the comparator 222 terminates the flow of current through the diode 90 through the inverter and level-shift circuit 142 and current-limit and voltage-regulation circuit 148. At the same time, the negative-going trailing edge at the output of the comparator 222 is inverted by transistor 262 to produce a positive-going pulse that is applied to the tone extender 166. The positive-going pulse is differentiated by capacitor 384 and resistor 386, and applied to the positive input of comparator 388 through resistor 390. The time constant of the capacitor 384 and resistor 386 is selected so that the positive input to the comparator 388 is positive for approximately 300 milliseconds. The resulting 300-millisecond, positive-going pulse at the output of the comparator 388 is applied through diode 392 to the tone generator 146. The tone generator 146 is powered by the positive supply voltage through voltage divider resistors 394, 396. Thus, when the flow of current to the diode 90 in the probe 22 is terminated, comparator 388 generates a 300-millisecond, positive-going pulse that causes the tone generator 146 to generate a 300-millisecond tone.

As explained above with reference to FIG. 5, the power supply and display unit 10 also incudes a short-circuit-sense and alarm circuit 170 that generates an audible tone when the inputs to the probe 22 have become short-circuited. The short-circuit-sense and alarm circuit 170 includes a comparator 400 that receives a reference voltage at its negative input through resistor 402 which is filtered by capacitor 404. The reference voltage is generated between the negative supply voltage and the normally positive output of the comparator 268 by voltage divider resistors 406, 408. The positive input of the comparator 400 is connected across the diode 90 of the probe 22 through diode 410. In the event that the voltage across the diode 90 falls below the reference voltage applied to the negative input of comparator 400, the output of comparator 400 goes negative. This negative output is applied through voltage divider resistors 412, 414 as positive feedback to the comparator 400 to maintain the output of the comparator 400 negative. Thus, the short-circuitsense and alarm circuit 170 will respond to intermittent shorts across the probe 22. The negative output of the comparator 400 is also applied to the positive inptu of comparator 268, thereby causing the output of comparator 268 to go negative and back-bias diode 276, thereby de-energizing the tone generator 146. The negative output from the comparator 268 also de-energizes the voltage regulator 290 through resistor 282 and diode 280. The low at the output of comparator 268 also allows capacitor 404 to discharge through resistors 402, 408. After a predetermined period, capacitor 404 has discharged to a voltage that is less than the voltage on the positive input of the comparator 400, thus causing the output of the comparator 400 to once again go positive. The positive output of the comparator 400 then causes the output of comparator 268 to once again go positive, and, if the inputs to the probe 22 are still short-circuited, the process will repeat itself. Thus, the short-circuit-sense and alarm circuit 170, in combination with the inverter and level-shift circuit 142, act as an oscillator. These circuits cause the power to be intermittently removed from the probe and the tone generator 146 to intermittently sound in the event that the inputs to the probe 22 are short-circuited.

To accommodate a tolerance violation in the avalanche breakdown voltage of diode 90 and to provide for changes in probe 22 size, a special probe 22 cable connector 415, containing resistors 414 and 413 was used.

Resistors 413 and 414 are contained inside cable connector plug 415 for probe 22. Resistor 414 is used to make a small modification in the power supply out-put voltage to match the small variation in avalanche breakdown of the diode 90 used with each cable connector 415.

Resistor 414 is connected in parallel with the current limit adjust resistor 300 and modifies the current limit for the particular size of probe 22 in use, less current limit for a small probe 22 and more current limit for a large probe 22.

A critical feature of the invention that is not apparent from either the block diagram of FIG. 5 or the schematic of FIG. 7 is the inherent temperature regulation of the cautery probe 22 without the use of complex and expensive feedback circuits. Specifically, the power supply and display unit 10 makes use of the inherent rise in the reverse breakdown or avalanche voltage of the diode 90 as a function of increasing temperature to provide inherent temperature regulation. It will be recalled that the power circuit of current throug the diode 90 is from the voltage regulator power transistor 150, potentiometer 300, and diode 90. In one operational embodiment, the voltage regulator 290 generates an output of 6.6 volts, which, with a −15 volt negative supply voltage, places 21.6 volts across the diode circuit. In the same embodiment, a Zener diode having a nominal voltage of 19.6 and a temperature coefficient of 0.015 volt per °C. is used. When the diode 90 is at ambient room temperature, there is thus approximately a 2-volt differential between the voltage across the diode and resistor 300 and the nominal breakdown voltage of the diode 90. A relatively low value resistor 300, such as 1 ohm, would thus allow 2 amps to flow through the diode 90. However, as the temperature of the diode 90 approaches a target temperature, such as 250° C., the reverse breakdown voltage of the diode 90 rises toward the 21.6 supply voltage, thus reducing the flow of current through the diode 90 and stabilizing its temperature. By appropriate adjustment of the potentiometer 300, the temperature of the probe 22 can be selected for a given set of cauterizing conditions without the need for expensive and complex voltage-sensing and feedback circuits.

Although the device described herein is principally designed for cauterization, it will be understood that it may also be used for other types of treatment. For example, it may be used to destroy superficial skin cancers without causing deep tissue damage. Consequently, the scope of the invention is not to be limited by the field to which the invention is applied.

We claim:

1. A thermal cautery system comprising:
   a thermal cautery probe having a heat-transfer portion adapted to be placed in contact with tissue to be cauterized;
   a diode mounted in said probe in thermal contact with said heat-transfer portion so that heat is transferred from said diode to said heat-transfer portion by conduction, said diode having a predetermined breakdown voltage at a predetermined temperature;
   a pair of electrical conductors; and
   a power supply connected to said diode through said electrical conductors, said power supply applying an output voltage to said diode that is substantially equal to the predetermined breakdown voltage of said diode at said predetermined temperature so that the current through said diode is substantially reduced as the temperature of said diode approaches said predetermined temperature.

2. The thermal cautery system of claim 1, further including a resistor connected in series between said power supply and said diode to limit the current through said diode to substantially the ratio of the difference between said output voltage and the reverse breakdown voltage of said diode to the resistance of said resistor.

3. The thermal cautery system of claim 1 wherein said pair of electrical conductors have a finite resistance, and wherein said power supply includes a compensating circuit adjusting the voltage that said power supply places across said conductors to compensate for the voltage drop in said conductors caused by current flowing through the resistance of said conductors.

4. The thermal cautery system of claim 3 wherein said compensating circuit comprises:
   a voltage regulator connected to said conductors, said foltage regulator applying a voltage across said conductors having a magnitude that is controllable by a signal applied to a control input of said voltage regulator;
   a current sensor operatively associated with at least one of said conductors, said current sensor generating an output indicative of the electrical current flowing through said conductors;
   an electrically conductive lead; and
   a control circuit connected to the output of said current sensor through said electrically conductive lead, said control circuit generating an output corresponding to the magnitude of the current flowing through said conductors, said output being applied to the control input of said voltage regulator to adjust the magnitude of the voltage that said voltage regulator applied across said conductors in proportion to the magnitude of the current flowing through said conductors.

5. The thermal cautery system of claim 1, further including audible tone generator means providing an audible indication when power is being applied to said probe, said system further including a tone extender circuit comprising timer means generating an output for a predetermined period after said timer means is triggered, said timer means having a trigger input receiving a triggering signal when power is removed from said probe, the output of said timer means energizing said tone generator means whereby said tone generator means continues to be energized for a predetermined period after power is removed from said probe to allow said probe to cool before the absence of said tone signals that said probe should be removed from said tissue being cauterized.

6. The thermal cautery system of claim 1 wherein said system includes current regulator means limiting the magnitude of the current flowing from said power supply to said diode, said current regulator means being disabled in response to receipt of a disable signal during a predetermined period after said power supply initially applies power to said diode, thereby allowing an unregulated flow of current through said diode during said predetermined period in order to maximize th initial heating of said probe.

7. A method of regulating the temperature of a thermal cautery probe having a diode in thermal contact with a heat transfer portion of said probe, said diode having a predetermined breakdown voltage at a predetermined temperature, said method comprising applying a voltage to said diode that is substantially equal to the predetermined breakdown voltage at said predetermined temperature so that the current through said diode is substanially reduced as the temperature of said diode approaches said predetermined temperature.

8. The method of claim 7 further including the step of limiting the flow of current through said diode to a predetermined value.

9. The method of claim 8 wherein said step of limiting the flow of current through said diode is provided by passing the current flowing through said diode through a resistor in series with said diode.

* * * * *

UNITED STATES PATENT AND TRADEMARK OFFICE
CERTIFICATE OF CORRECTION

PATENT NO. : 4,691,703

DATED : September 8, 1987

INVENTOR(S) : David C. Auth; Dale M. Lawrence; Tim R. Majoch

It is certified that error appears in the above—identified patent and that said Letters Patent is hereby corrected as shown below:

In claim 4, column 14, line 2, delete "foltage" and substitute therefor --voltage--.

In claim 6, line 9, delete "th" and substitute therefor --the--.

Signed and Sealed this

Fifth Day of April, 1988

Attest:

DONALD J. QUIGG

Attesting Officer

Commissioner of Patents and Trademarks